(12) United States Patent
Lovoi et al.

(10) Patent No.: US 10,076,274 B2
(45) Date of Patent: *Sep. 18, 2018

(54) SYSTEM AND METHOD FOR NON-INVASIVE DETECTION OF HUMAN CRANIAL CONDITIONS

(71) Applicant: JAN MEDICAL, INC., Mountain View, CA (US)

(72) Inventors: Paul A Lovoi, Saratoga, CA (US); Kieran Murphy, Baltimore, MD (US); Jeff Jarvela, San Jose, CA (US); Pete Neild, Poway, CA (US); John Thomas, San Diego, CA (US); Ray Schumacher, La Jolla, CA (US); Charlie Macvean, San Diego, CA (US)

(73) Assignee: JAN MEDICAL, INC., Munich (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/288,395

(22) Filed: Oct. 7, 2016

(65) Prior Publication Data
US 2017/0020435 A1    Jan. 26, 2017

Related U.S. Application Data

(63) Continuation-in-part of application No. 14/565,337, filed on Dec. 9, 2014, which is a continuation-in-part
(Continued)

(51) Int. Cl.
*A61B 5/00* (2006.01)
*G16H 50/70* (2018.01)
(Continued)

(52) U.S. Cl.
CPC ............ *A61B 5/4064* (2013.01); *A61B 5/024* (2013.01); *A61B 5/7282* (2013.01); *A61B 7/00* (2013.01);
(Continued)

(58) Field of Classification Search
CPC ..... A61B 7/04; A61B 5/02007; A61B 5/0205; A61B 5/4064; A61B 5/4076;
(Continued)

(56) References Cited

U.S. PATENT DOCUMENTS 5,074,310 A * 12/1991 Mick ................. A61B 5/031
600/561
5,117,835 A * 6/1992 Mick ................. A61B 5/0051
600/561
(Continued)

OTHER PUBLICATIONS

Memsic (Accelerometer spec sheet, http://search.alkon.net/cgi-bin/pdf.pl?pdfname=memsic/mxa6500ep.pdf, Mar. 22, 2005).*
(Continued)

*Primary Examiner* — Amelie R Gillman
*Assistant Examiner* — Carolyn Pehlke
(74) *Attorney, Agent, or Firm* — Tucker Ellis LLP (57) ABSTRACT

Vascular conditions are detected non-invasively in the human body using a collection of information from small local regions of the vasculature. An array of accelerometers are attached to the head and blood flow sounds are recorded. Vibration signatures of vessel structures such as branches, aneurysms, stenosis, etc. using random, periodic, band limited or transient analysis provides a signature library for further processing. The signature library is used to localize the origin of recognized vascular features and the localized feature is presented to the physician in a clinically relevant manner.

18 Claims, 10 Drawing Sheets

Related U.S. Application Data of application No. 11/894,052, filed on Aug. 17, 2007, now Pat. No. 8,905,932.

(60) Provisional application No. 60/838,624, filed on Aug. 17, 2006.

(51) Int. Cl.

| | | |
|---|---|---|
| *G16H 50/20* | (2018.01) | |
| *G16H 50/50* | (2018.01) | |
| *A61B 7/00* | (2006.01) | |
| *G06K 9/00* | (2006.01) | |
| *A61B 5/024* | (2006.01) | |
| *G01H 1/00* | (2006.01) | |
| *A61B 5/11* | (2006.01) | |
| *A61B 5/02* | (2006.01) | |
| *A61B 5/0205* | (2006.01) | |
| *A61B 7/04* | (2006.01) | |
| *G06F 19/00* | (2018.01) | |

(52) U.S. Cl.
CPC .............. *A61B 7/04* (2013.01); *G06F 19/324* (2013.01); *G06K 9/0055* (2013.01); *G16H 50/20* (2018.01); *G16H 50/50* (2018.01); *G16H 50/70* (2018.01); *A61B 5/0205* (2013.01); *A61B 5/02007* (2013.01); *A61B 5/1102* (2013.01); *A61B 5/4076* (2013.01); *A61B 5/6814* (2013.01); *A61B 5/7246* (2013.01); *A61B 5/7257* (2013.01); *A61B 5/7267* (2013.01); *A61B 5/7275* (2013.01); *A61B 2562/0219* (2013.01); *G01H 1/00* (2013.01)

(58) Field of Classification Search
CPC ..... A61B 5/6814; A61B 5/7267; A45C 11/38; A45C 13/126; F16D 3/16; F16D 3/2055; F16D 3/43; G06F 19/324; G06F 19/3437; G06F 19/3443; G06F 19/345; G06K 9/0055

See application file for complete search history.

(56) References Cited

U.S. PATENT DOCUMENTS

| | | |
|---|---|---|
| 6,024,701 A | 2/2000 | Almog |
| 8,905,932 B2* | 12/2014 | Lovoi ............... A61B 5/02007 600/438 |
| 2002/0067107 A1 | 6/2002 | Lewis |
| 2002/0077567 A1 | 6/2002 | McLeod |
| 2006/0100530 A1 | 5/2006 | Kliot |
| 2009/0012430 A1 | 1/2009 | Lovoi |
| 2013/0267858 A1 | 10/2013 | Berkow et al. |

OTHER PUBLICATIONS

Guevara, Miguel Angel, and María Corsi-Cabrera. "EEG coherence or EEG correlation?." International Journal of Psychophysiology 23.3 (1996): 145-153.*

Kurtz, Kenneth J. "Bruits and hums of the head and neck." (1990).*

Jervis, B. W., L. Smaglo, and S. Djebali. "The rapid classification of brain conditions using neural networks." (2001): 4-4.*

Kosugi, Yukio, et al. "Detection and analysis of cranial bruit." IEEE transactions on biomedical engineering 3 (1987): 185-191.*

United States Patent Office, International Searching Authority, International Search Report and Written Opinion dated May 19, 2016 for International Patent Application No. PCT/US2015/064840, 14 Pages.

* cited by examiner

TRIGGER PULSE

|   | $S_1$ | $S_2$ | $S_3$ | $S_4$ | I |
|---|---|---|---|---|---|
| A | 10 | 25 | 50 | 54 | 1 |
| B | 15 | 24 | 47 | 51 | 5 |
| C | 18 | 22 | 44 | 46 | 10 |
| D | 24 | 23 | 39 | 42 | 5 |
| E | 28 | 24 | 35 | 36 | 1 |

FIG. 21

SYSTEM AND METHOD FOR NON-INVASIVE DETECTION OF HUMAN CRANIAL CONDITIONS

CLAIM OF PRIORITY

The present application is a continuation-in-part of application Ser. No. 14/565,337 filed Dec. 9, 2014, which is a continuation-in-part of application Ser. No. 11/894,052, filed Aug. 17, 2007, now U.S. Pat. No. 8,905,932, which claims benefit of priority from provisional application No. 60/838,624, filed Aug. 17, 2006.

FIELD OF THE INVENTION

The invention concerns detection of conditions of human vasculature non-invasively.

BACKGROUND

Stroke is a manifestation of injury to the brain which is commonly secondary to atherosclerosis or hypertension, and is the third leading cause of death in the United States. Stroke can be categorized into two types, ischemic stroke and hemorrhagic stroke. Additionally, a patient may experience transient ischemic attacks, which are in turn a high risk factor for the future development of a more severe episode.

Examples of ischemic stroke encompass thrombotic, embolic, lacunar and hypo-perfusion types of strokes. Thrombi are occlusions of the arteries created in situ within the brain, while emboli are occlusions caused by material from a distant source, such as the heart and major vessels, often dislodged due to myocardial infarct or atrial fibrillation or carotid disease or surgical or percutaneous intervention. Thrombi or emboli can result from atherosclerosis or other disorders, for example arteritis, and lead to physical obstruction of arterial blood supply to the brain. Lacunar stroke refers to an infarct within non-cortical regions of the brain. Hypo-perfusion embodies diffuse injury caused by non-localized cerebral ischemia secondary to low cerebral perfusion, typically caused by myocardial infarction, arrhythmia, blood loss or prolonged low blood pressure.

Hemorrhagic stroke is caused by intra cerebral or subarachnoid hemorrhage, i.e., bleeding in to brain tissue, following blood vessel rupture within the brain or venous thrombosis. Intra cerebral and subarachnoid hemorrhages are subsets of a broader category of hemorrhage referred to as intracranial hemorrhage.

Intra cerebral hemorrhage is typically due to chronic hypertension and a resulting rupture of an arteriosclerotic vessel. Stroke-associated symptom(s) of intra cerebral hemorrhage are abrupt, with the onset of headache and steadily increasing neurological deficits. Nausea, vomiting, delirium, paralysis, seizures and loss of consciousness are additional common stroke-associated symptoms.

In contrast, most subarachnoid hemorrhage is caused by head trauma or aneurysm rupture which is accompanied by high-pressure blood release which also causes direct cellular trauma. Prior to rupture, aneurysms may be asymptomatic, or occasionally associated with headaches. However, headache typically becomes acute and severe upon rupture and may be accompanied by varying degrees of neurological deficit, vomiting, dizziness, and altered pulse and respiratory rates, photophobia and severe headache and or neck stiffness.

Current diagnostic methods for stroke include costly and time-consuming procedures such as non-contrast computed tomography (CT) scans, electrocardiogram, magnetic resonance imaging (MRI) and angiography. Determining the immediate cause of stroke is difficult. CT scans can detect parenchymal bleeding greater than 5 mm and 95% of all subarachnoid hemorrhages. CT scans often cannot detect ischemic strokes until 6 hours from onset, depending on infarct size. CT only identifies 48% of acute strokes in the first 48 hours. MRI may be more effective than CT scan in early detection of ischemic from hemorrhagic stroke, and is not widely available. Angiography is a definitive test to identify stenosis or occlusion of large and small cranial blood vessels, and can locate the cause of subarachnoid hemorrhages, define aneurysms, and detect cerebral vasospasm. It is, however, an invasive procedure and is also limited by cost and availability.

Immediate diagnosis and care of patients experiencing stroke can be critical. For example, tissue plasminogen activator (tPA) given within three hours of symptom onset in ischemic stroke is beneficial for selected acute stroke patients. In contrast, thrombolytics and anticoagulants are strongly contraindicated in hemorrhagic strokes. Thus early differentiation of ischemic events from hemorrhagic events is imperative. Moreover, delays in confirmation of stoke diagnosis and identification of stroke type limit the number of patients that may benefit from early intervention therapy. In addition, continuous monitoring of stroke patients is not possible with CT or MRI scanners, thus only one snapshot in time is available for diagnosis and treatment. Clinical observations are the basic tool that is used to monitor the progress of stroke patients.

Early detection of an aneurysm is beneficial as it can frequently be treated either by a surgical procedure of clip occlusion or by endovascular coil embolism. Presently, approximately three quarters of patients are treated with clip occlusion, the remainder with endovascular coil embolism. Either surgery, particularly the endovascular procedure, can by performed with low complication rate and high rate of success.

Once an aneurysm ruptures, however, the patient declines rapidly due to major brain injury, and over 50% of aneurysm rupture patients die acutely. Thus detection of at risk aneurysms is of great benefit. A physician faced with possible aneurysm warning signs must judge whether the symptoms warrant the trauma, expense and morbidity of contrast angiography.

Ferguson, in J. Neurosurg. 36:560-563 (1972), suggested detecting aneurismal signals by recording sounds from aneurysms exposed at operations using a cardiac phono-catheter. Kosugi et al., in Stroke 14 (1) 37-42 (1983), disclosed the use of a "cement wall microphone", (contact accelerometer) in contact with the cranium and the teeth in an attempt to detect aneurysms.

However, devices and methods to date have not localized the detected vascular conditions and do not present the collected data in a clinically useful way.

Thus, despite these known devices, there remains a need for an acoustic detector that is designed to more effectively record, analyze, localize and present, in a clinically useful manner, cerebral arterial and venous conditions.

SUMMARY OF THE INVENTION

The invention concerns detection of conditions of human vasculature non-invasively, from outside the body, and in particular, locating aneurysms, partial or complete stenoses, ruptures, peripheral bleeding, and other abnormal conditions pertaining to the cerebral vasculature, profiling blood or other fluid flow through or around the cerebral vasculature, and mapping to provide a spatially resolved characterization of the major vasculature within the head.

This application describes a system and method for detecting a vascular condition non-invasively in the human body, by a collection of signal information from local, small regions of the vasculature. This is accomplished in a preferred embodiment by attaching, or contacting an array of accelerometers, or other sensors, to the head of a patient and recording vibration signals. The vibration signatures of blood vessel structures such as branches, aneurysms, stenosis or other structures using random, periodic, band limited or transient analysis provide a library for further processing.

The library becomes part of a cerebral modeling arithmetic computer using basis functions, or other artificial neural network. The developed signature library is then used to facilitate localizing the origin of the recognized vascular feature; the localized feature is then presented to the physician in a clinically relevant manner.

The data to build the neural network (NN) and/or data store for correlation are obtained by acquiring data from patients with known pathologies as well as controls, and optionally with studies of constructed or cadaver vasculatures. The data are formatted according to the requirements of each processing method before being used for training or algorithm construction.

In an embodiment, this application describes a noninvasive method for differentiating ischemic from hemorrhagic stroke and for continuously monitoring the condition of stroke patients by providing clinically useful localized information. It is also the purpose to monitor or screen high risk patients to detect conditions that may lead to a first or subsequent stroke.

Other objects and advantages of the present invention will become apparent to those skilled in the art from the following description of the various embodiments, when read in light of the accompanying drawings.

BRIEF DESCRIPTION OF THE DRAWINGS

Various embodiments of the present invention can be described in detail based on the following figures, wherein.

DETAILED DESCRIPTION

In the following description, the invention will be illustrated by way of example and not by way of limitation in the figures of the accompanying drawings. References to various embodiments in this disclosure are not necessarily to the same embodiment, and such references mean at least one. While specific implementations are discussed, it is understood that this is provided for illustrative purposes only. A person skilled in the relevant art will recognize that other components and configurations may be used without departing from the scope and spirit of the invention. Furthermore, in certain instances, numerous specific details will be set forth to provide a thorough description of the invention. However, it will be apparent to those skilled in the art that the invention may be practiced without these specific details. In other instances, well-known features have not been described in as much detail so as not to obscure the invention.

General Outline of Process

Periodic pulses from the heart produce waves of expanding blood vessels within the body. The tissue surrounding the blood vessels is displaced during the pulse and contracts again after the pulse. This displacement propagates outward from the blood vessel. In the case of the brain, this displacement reaches the skull and displaces the bone in response the displacement of the blood vessel wall. Extremely sensitive accelerometers record this displacement. The accelerometers are very sensitive, typically 500 mV/g or more. Such an accelerometer is a model from DYTRAN of California.

The character of the signal recorded by the accelerometers is dependent on the nature of the displacement caused by the blood pulse. At a restriction in a blood vessel the displacement before the restriction is larger than it would be without the restriction and the displacement beyond the restriction is less. The spatial distribution of displacement produces a different signature than that recorded by an unrestricted vessel. Likewise an aneurysm allows a circulation of blood within the bulb of the aneurysm during the pulse and produces a periodic signal that modifies the displacement signal. Other geometric arrangements of vessels likewise produce unique signatures in displacement.

The use of accelerometers overcomes limitations of acoustic signal detectors (e.g. microphones). Accelerometers have a distinct advantage over microphones since microphones require acoustic signals to propagate through the soft tissue of the brain, conduct through the hard bone of the skull, again transfer to the soft tissue of the skin and finally be transferred to the microphone. Microphones have been most successful when attached to the teeth, positioned within the ear or focused on the eye sockets. Thus the use of microphones has been more successful when they can either have direct bone contact or look where there is no skull present. In comparison, Accelerometers measure the displacement of the entire skull structure.

The use of accelerometers also eliminates external sources of signal. The microphone is also very sensitive to sound signals produced from outside the body, such as sirens, talking, doors slamming and other sound signals. In comparison. Accelerometers are much less sensitive to acoustic signals and generally are only sensitive to signals along the primary axis of the detector.

Localization with Phase. The use of multiple accelerometers positioned around the head allows signals from different parts of the brain to be distinguished by location. Beyond just the relative magnitude of the signals from each of the sensors, the phase relationship of the signals between sensors is used to determine the location of the displacement source. Since there are a multitude of signals produced during the pulse, from different spatial positions, and with the pulse traveling from the proximal to distal portions of the vasculature, a means to distinguish each of these signals is needed. This differentiation is accomplished by using a priori information about the head and the approximate positions of each of the accelerometers. For example signals cannot emanate from locations outside of the head nor at times that are not related to the blood pulse.

Timing for Localization. A gating sensor, an EKG electrode 116 (See FIG. 1), is used to provide timing information to the system. Since the heart rate varies in a given person both at rest and with exertion, the timing signal is used as an approximate starting point for timing the signal arrival at the sensors but cannot determine the pulse timing. Leeway is still needed as the intra-pulse timing may be increasing or decreasing for each pulse.

Localization Example: Signals data are captured from multiple sensors 110 (See FIGS. 1 and 3) during a pulse. The signals from the multiple sensors are shifted in time by a guessed amount and then added together. The resulting signal is then analyzed either by direct amplitude, by Fourier transform or by another algorithm. This process is continued over the valid range of phases from each sensor.

If a given signal is correlated with the signal from another sensor then the resulting combined signal will have an enhanced signature when the phases represent the location of the signal and not for surrounding phases within the allowable phase space. The quality of a signature can be quantified and that quantification can be established for each phase shift between sensors. As the phase is shifted over the possible range the figure of merit (quantified result of a single phase relationship) will increase and decrease. The peaks represent recognized signatures at localized positions.

While this process is straightforward it is very processor intensive. The allowable phase shifts for all the sensors can be calculated beforehand and this range used to limit the correlation space. The computational problem can be parsed such that parallel processors tackle the problem in parallel thus reducing the time from data collection to data presentation.

It is important to note that once the initial data has been analyzed the relative phase between sensor data for the many signals within the brain is known, continued analysis of captured data is much less computational intensive. This a priori knowledge vastly reduces the computational requirements of the system and allows near real time presentation of the data. Current computers are certainly capable of completing the vast amount of computations in times suitable for clinical use and this will just improve as the speed and processing throughput of computers increases.

Creation of Synthetic Image: The data needs to be presented in a recognized manner for the clinician to make use of it. By the nature of the data capture and processing, the most prominent structures are most readily identified and localized. This is not a complete map of the brain vasculature. Using a priori knowledge of the typical structure of the vasculature (and noting that there are significant deviations from the "typical" structure) the identified structures can be placed onto a cartoon of the entire vasculature, replacing the typical cartoon representations with improved representations based on the data analysis. This synthetic image is then presented to the clinician; as a 3D representation, a simulated CT or MRI scan or as an angiogram. As data continues to be acquired and processed the synthetic image can be updated.

Neural Network: The array of different accelerometer signatures produced by features within the vasculature is quite large due to the variable physiology of patients but there are generally only a few major underlying features. This type of data is ideal for using neural networks to identify the features causing the signature to be categorized. As the library of unique features and the associated signatures grows the neural network will improve in correctly identifying features in patients. Neural networks typically are trained by inputting a set of known inputs and known outputs and allowing the weights of the neural connections to change to optimize the matching of the inputs and outputs. When a new input is presented to the neural network the output closest to the input is given the highest output even if the input is not a perfect match to any of the training set.

Beam Forming: In a process similar to localization previously discussed, beam forming varies the phase between data produced by different sensors. It is the purpose of beam forming to systematically vary the phase and retain the resulting signal. With small steps in the phase a very high spatial resolution map of the vasculature is produced. Beam forming is used when a feature of interest is localized and more detailed information is desired about that feature. Beam forming is computationally intensive but lends itself to parallel processing and will be aided by improvements in processing power of both general purpose and special purpose processors.

Figure 1:
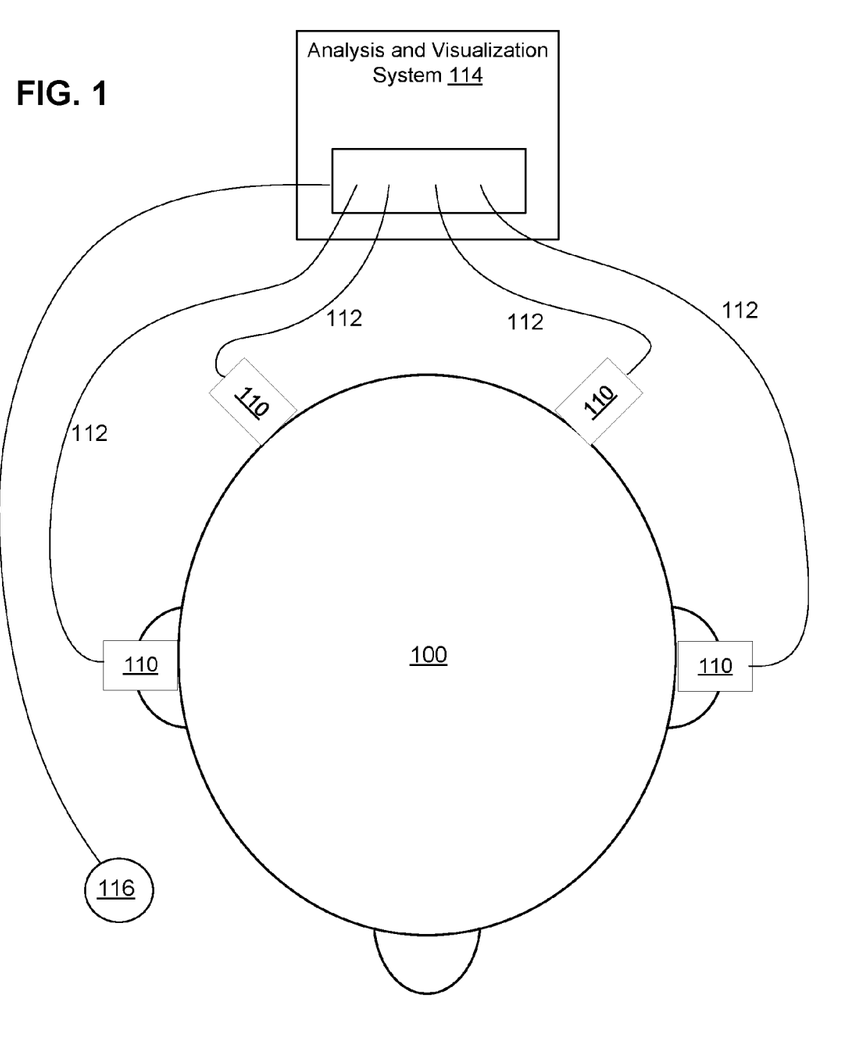
FIG. 1 is a plan view of sensors on a head.

FIG. 1 is a plan view of sensors 110 on a head 100. FIG. 1 shows a patient with sensors 110 attached to various places on the head 100. The sensors 110 are attached by cables 112, but could be connected wirelessly, to the analysis and visualization portion of the system 114.

Figure 2A:
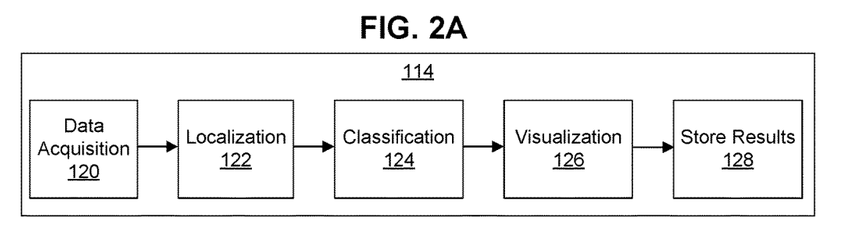
FIG. 2A is a block diagram of the steps of the invention.

FIG. 2A shows a block diagram of the analysis and visualization portion of the system 114. The analysis and visualization portion of the system 114 includes data acquisition block 120, localization block 122, classification block 124, visualization block 126, and results storage block 128. The signal arrives from each sensor 110 and is conditioned and processed in the data processing block. The processed signal is digitized and processed in parallel. Processors analyze the signal for matches to library conditions and identify matches multiple sensors to localize the source of the matched signal. This process is repeated for each identified signal both by and for multiple locations. The collection of all the localized and identified data is processed by the image database for presentation. The digitized input signal is also stored in the array data memory for further analysis. Localized features can be further characterized by using beam forming techniques.

Figure 2B:
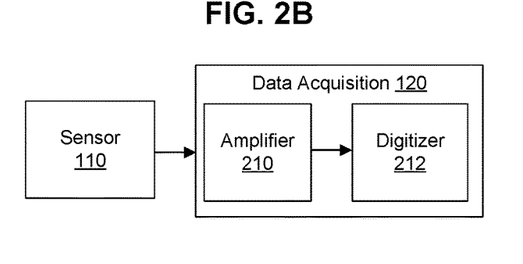
FIG. 2B is a block diagram of the sensor processing steps.

FIG. 2B is a block diagram of the sensor processing steps. FIG. 2B is a more detailed block of the sensor 110 and data acquisition block 120 in FIGS. 1A and 1B. As shown in FIG. 2A, the sensor signal is amplified by amplifier 210 and possibly filtered, sometimes dynamically, before being amplified and finally digitized by digitizer 212. The signals from each of the sensors 110 in FIG. 1A are digitized maintaining the time relationship between each sensor 110.

Figure 2C:
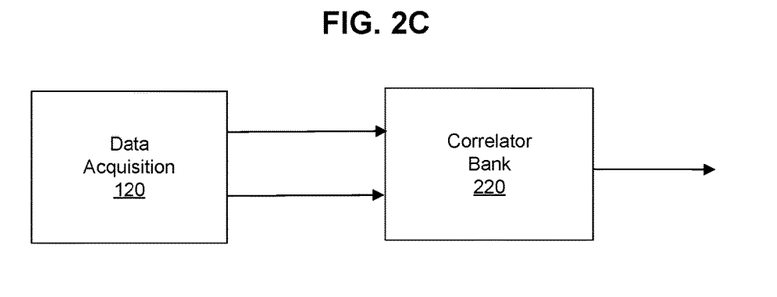
FIG. 2C is a diagram of the correlation circuit.

FIG. 2C is a diagram of the correlation circuit. FIG. 2C shows a block diagram of the correlator bank 220 that localizes the signals from the sensors 110. All the sensor signals, with their timing information, are fed into to the correlator bank 220. The correlator bank 220 determines, by changing the time relationship between different sensor signals, when two signals are from the same source and record those time relationships. Multipath rejection via modeling of the signal phase delay of the skull (or body) may be used to improve accuracy of the algorithms. The relative attenuation of the intervening materials may also be used. The signal that is common to the multiple sensor signals is recorded as the signal that was created at the location that is determined by the time differences between the arrivals of the signal at each sensor 110, as will be further explained below.

Figure 3:
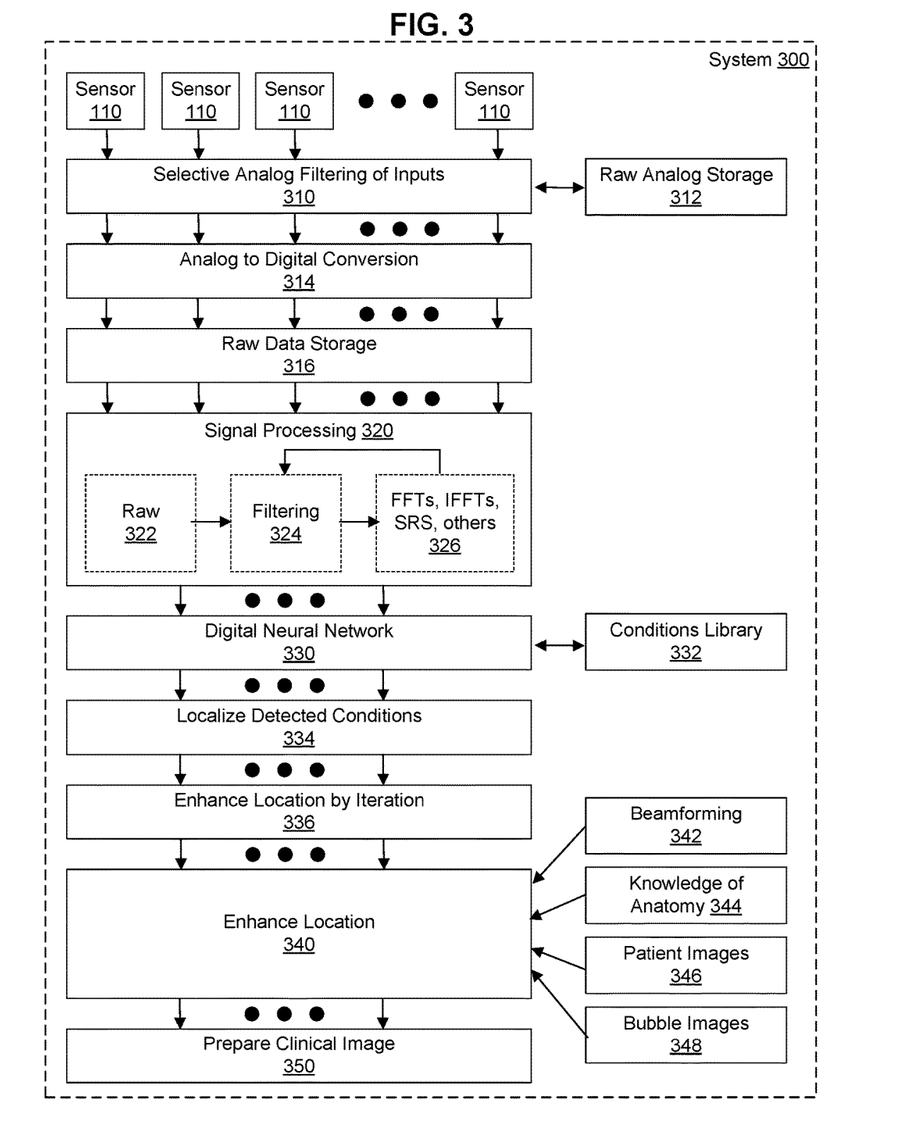
FIG. 3 is a flow diagram outlining the overall system.

FIG. 3 is a flow diagram outlining the overall system 300. As shown in FIG. 3 signals from a plurality of sensors 110 are provided to block 310 for selective analog filtering of inputs. Analog signals may also be stored or retrieved in block 312. The output of block 310 is provided to block 314 for analog to digital conversion. The output of block 314 is provided to block 316 for raw data storage. The output of raw data storage 316 is provided to signal processing block 320.

In signal processing block 320, raw data 322 undergoes filtering 324 and analysis using FFTs, iFFTs, SRS or other techniques with the results fed back to the filtering block 324. The output of the signal processing block 320 is provided to digital neural network 330. The processed signal is digitized and processed in parallel through the neural net 330. Digital neural network 330 can also store conditions to or retrieve conditions from condition library 332. The output of digital neural network 330 is provided to block 334 to localize detected conditions and block 336 to enhance localization by iteration.

The output of block 336 is provided to enhance location block 340 which may make use of beamforming 342, knowledge of anatomy 344, patient images (CT, MRI, Contrast, Angio.) 346, and/or bubble images 348. The output of enhance location block 340 is provided to block 350 to prepare a clinical image.

Some of the features of the system as represented in FIG. 3 are:
 The use of noise cancellation;
 The elimination of overriding signals;
 The localizers for each signal type;
 The use of the raw data memory;
 The causal network;
 The patient factors input and how it is used;
 The image database;
 The image; and
 The dynamic filtering and its purpose.

Figure 4:
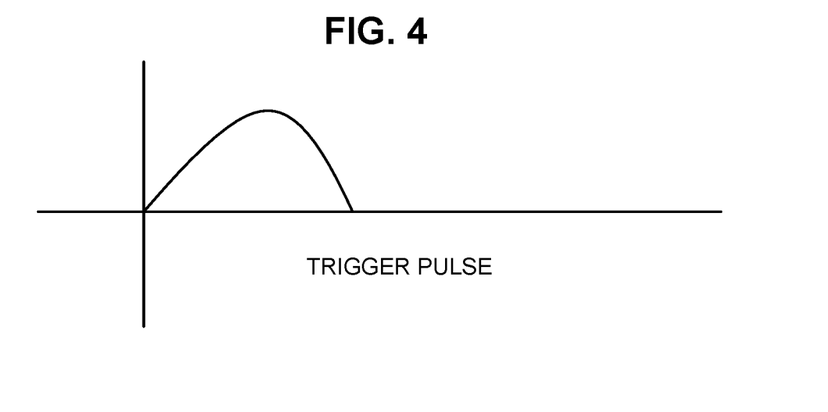
FIG. 4 is a diagram of a trigger pulse amplitude VS time.
Figure 5:
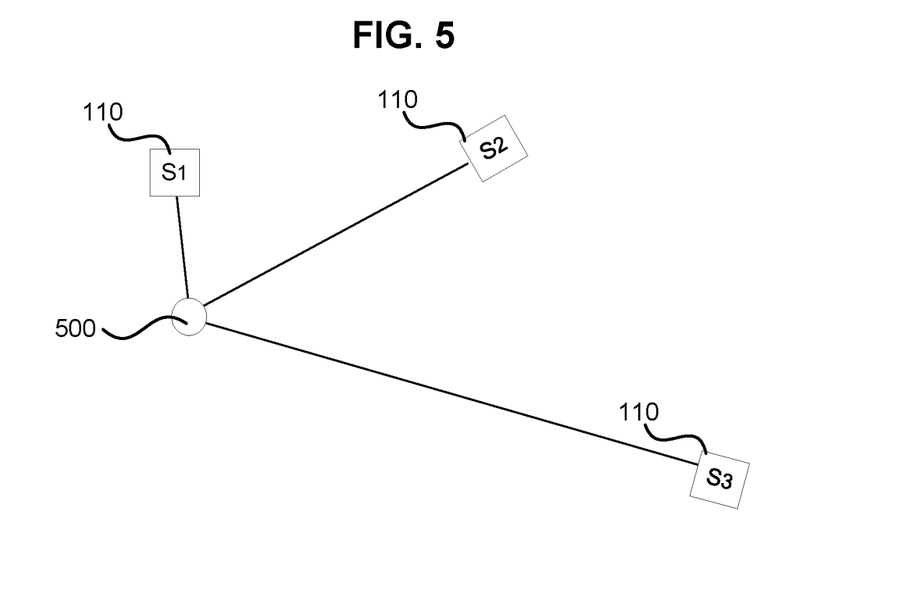
FIG. 5 is a diagram of sensors at various distances from a pulse source.
Figure 6:
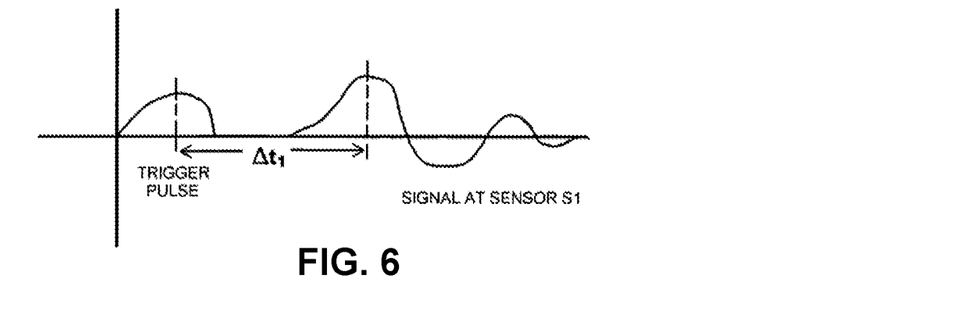
FIG. 6 is a diagram of a trigger pulse and a received pulse at a distant sensor.
Figure 7:
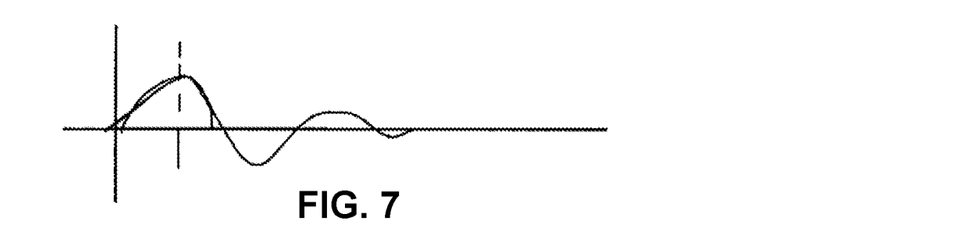
FIG. 7 is the overlay of the trigger pulse and the received pulse shifted by time delta t1.
Figure 8:
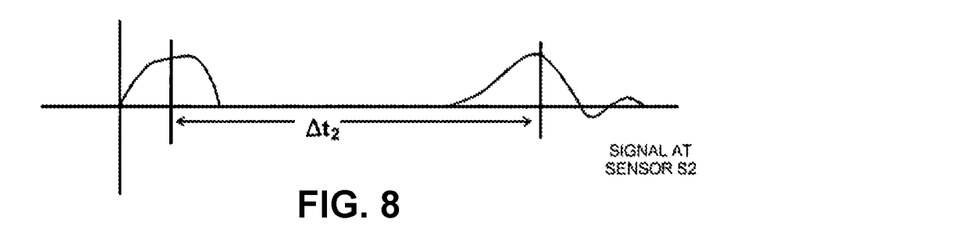
FIG. 8 is a diagram of a trigger pulse and a received pulse from a further sensor.
Figure 9:
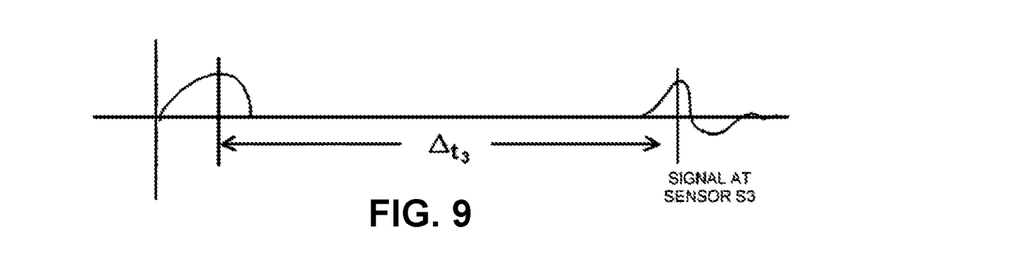
FIG. 9 is a diagram of a trigger pulse and a received pulse from the furthest sensor.
Figure 10:
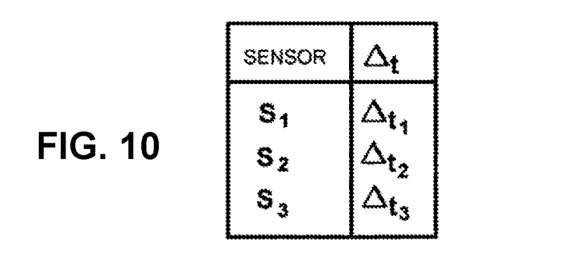
FIG. 10 is a table the time of first signal arrival from the trigger pulse for each sensor.

FIG. 4 shows a simple trigger pulse test source signal in amplitude versus time. FIG. 5 shows a diagram of the location of a signal source 500 and three sensors (110) S1, S2 and S3, shown at different distances from the signal source 500. FIG. 6 shows a time vs amplitude waveform of the trigger pulse and the arrival of the signal at sensor S1. The time that the signal takes to arrive at sensor S1 is delta t1. FIG. 7 shows the superposition of the two signals in FIG. 6 translated in time by delta t1. FIG. 8 shows the same data as FIG. 6 but for sensor S2 that is farther from the source than sensor S1. The time for the signal to arrive from the source at sensor S2 is delta t2. FIG. 9 shows that same data as FIGS. 6 and 8 but for sensor S3 with a transit time of delta t3. FIG. 10 is a table with the arrival time for the signal for each of the sensors, S1, S2 and S3.

Figure 11:
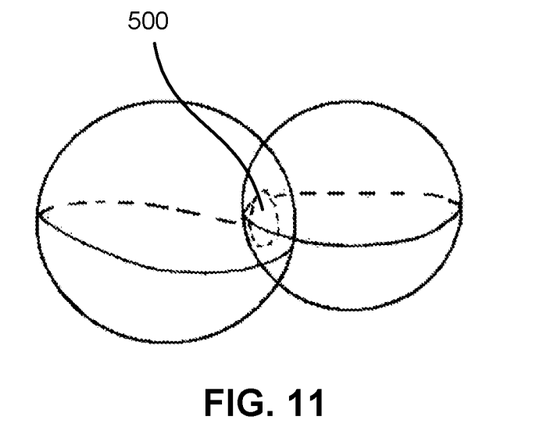
FIG. 11 is a diagram of two intersecting spheres of different diameters.
Figure 12:
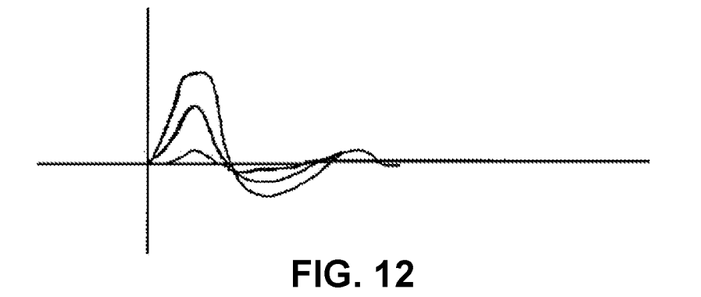
FIG. 12 is a diagram of three sensor signals shifted according to the table in FIG. 10.
Figure 13:
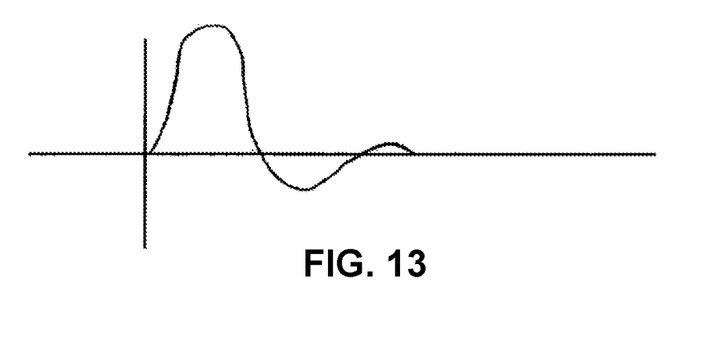
FIG. 13 is a diagram of the sum of the three sensor signals in FIG. 12.

FIG. 11 shows two different radius intersecting spheres with the dotted line showing the locus of points where the distance between the centers of sphere 1 and sphere 2 are constant. This locus of points represents the possible position of the source 500 based on only the signal from two sensors. Adding a third sensor, not shown, would restrict the location of the source to a single location, thus fixing its location with respect to the three sensors. FIG. 12 shows all the sensor signals from FIGS. 6, 8 and 9 translated by the times listed in FIG. 10. FIG. 13 shows the sum of the three signals shown in FIG. 12.

Figure 14:
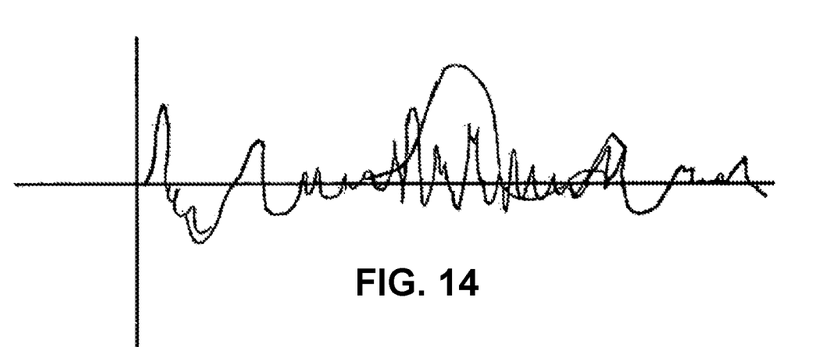
FIG. 14 is a received sensor signal as shown in FIG. 6 and typical noise signal.
Figure 15:
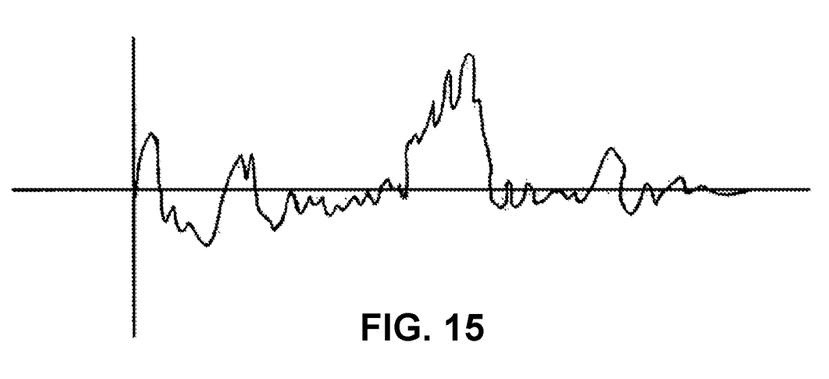
FIG. 15 is a diagram of the sum of the noise signal and the signal from sensor 1.
Figure 16:
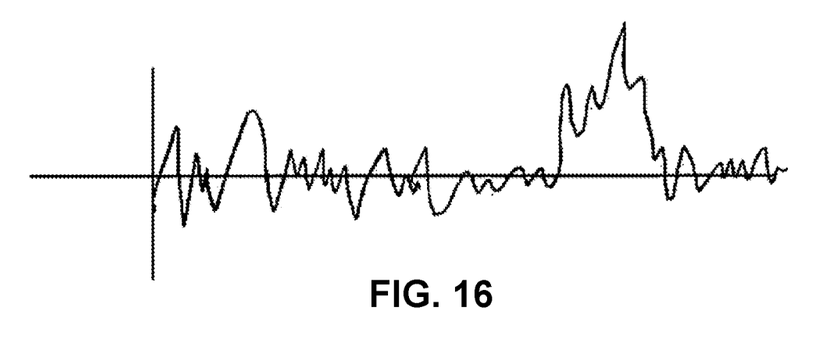
FIG. 16 is a diagram of the sum of noise signal and the signal from sensor 2.
Figure 17:
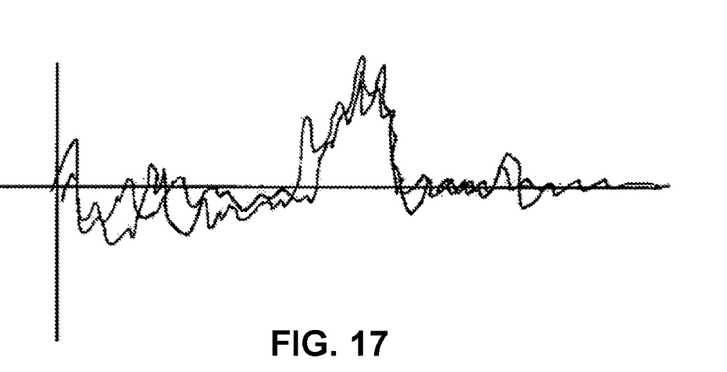
FIG. 17 is a diagram of the superposition of the noise signals from each of the three sensors.
Figure 18:
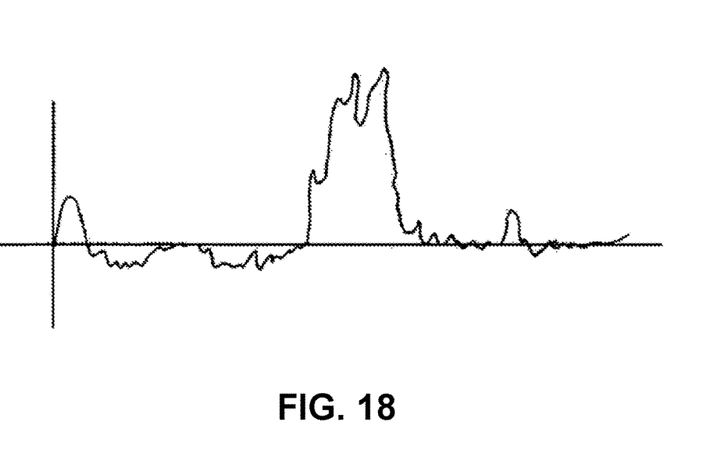
FIG. 18 is a diagram of the sum of the noise signals from each of the three sensors.

FIG. 14 shows the typical signal noise that might be expected to be present on the sensor signal along with the sensor signal as shown in FIG. 6. FIG. 15 shows how the sensor signal in FIG. 14 would look for a typical signal noise environment. FIG. 16 shows the same signal as FIG. 15 but for sensor S2 rather than sensor S1. FIG. 17 schematically shows superposition of the noisy signals from all the sensors, translated by the times shown in the table in FIG. 10. FIG. 18 shows the sum of all the signals in FIG. 17 with the noise reduced due to the summing of random noise and the signal increased by the superposition of the common signal.

Figure 19A:
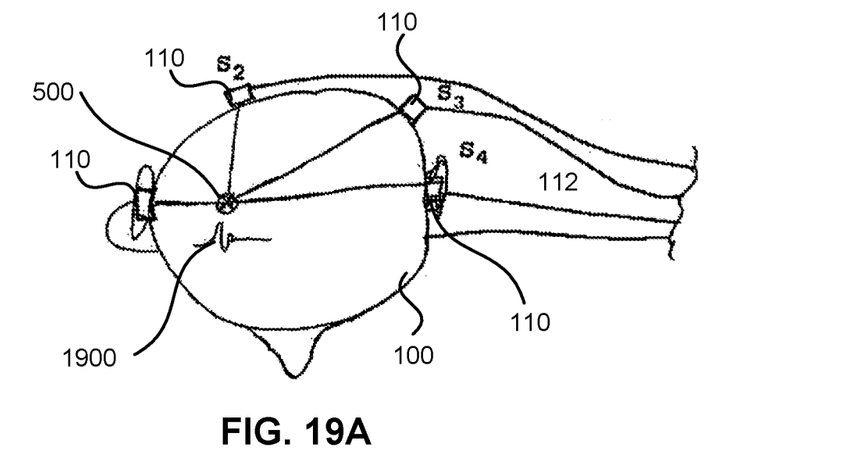
FIG. 19A is a plan view in one plane of four sensors on a human head with the distances from a noise source to each sensor.

FIG. 19A is a plan view in one plane of four sensors on a human head 100 with the distances from a noise source to each sensor 110. FIG. 19A is a pictorial plan view diagram of a patient with sensors (110) S1 through S4 attached to the head 100. A signal source 500 at X is located at distances D1 through D4 from the respective sensors 110. A waveform 1900 is shown at X depicting the acoustic signature that is emitted at location X.

Figure 19B:
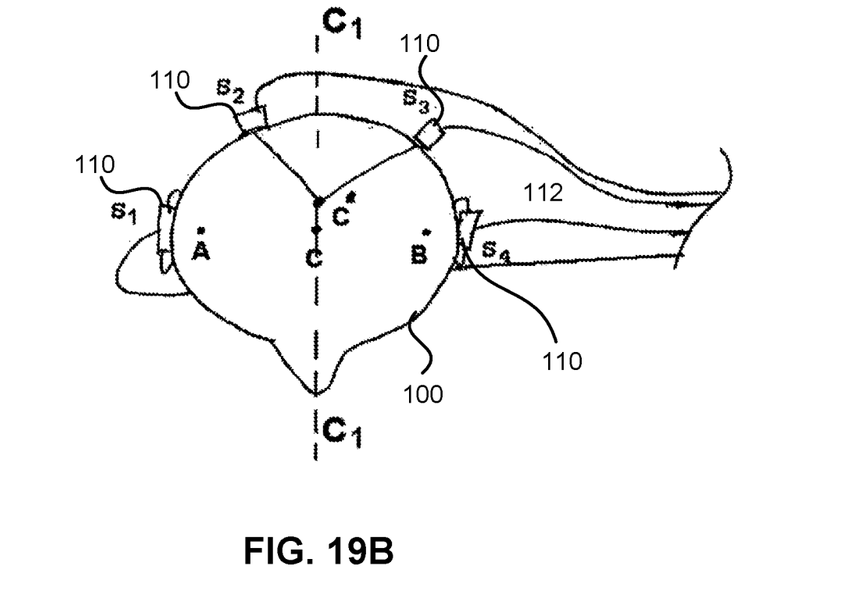
FIG. 19B is a plan view in one plane of four sensors on a human head with several possible sources of sound indicated.

FIG. 19B is a plan view in one plane of four sensors on a human head with several possible sources of sound indicated. FIG. 19B is a schematic pictorial diagram of a patient as in FIG. 19A. Four locations within the head 100 of the patient are shown; points A, B C and C'. A centerline of symmetry is shown with point C' lying on the centerline and equal distance from sensors S2 and S4. Point C is also on the centerline and a short distance from point C'. Small changes in the distances D2 and D3 represent the small distance from C' to C. Beamforming techniques depend on changing the phase relationship between data collected by the sensors 110 in a precise and controlled way, such as represented by the example in FIG. 19B.

Figure 20:
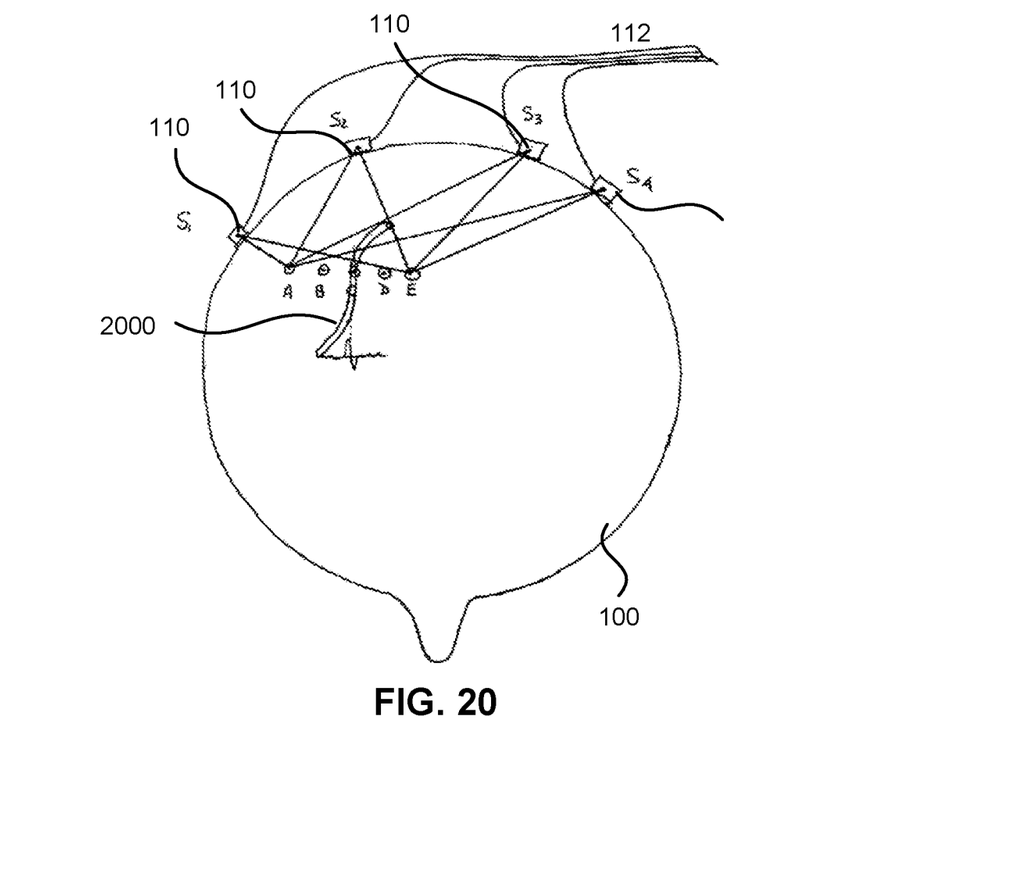
FIG. 20 is a plan view of the head with sensors shown and the geometry of beam forming.

FIG. 20 is a plan view of the head with sensors shown and the geometry of beam forming. FIG. 20 shows a pictorial diagram of a patient with sensors S1 through S4 as is shown in FIG. 19A with the additional points A-E shown. Points A through E represent small steps across a point of interest, as depicted by a segment of vessel 2000 shown across the points A-E. The distances from each point A-E to each sensor S1-S4 are different and are shown in the table in FIG.

Figure 21:
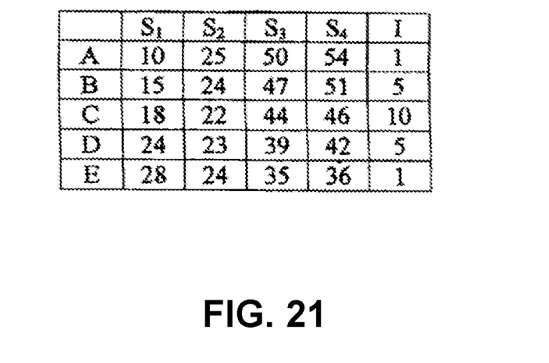
FIG. 21 is a table giving the distances for four sensors and five beam forming position.

21. FIG. 21 is a table giving the distances for four sensors and five beam forming position.

Ultrasound Bubbles

Ultrasound contrast agents are materials that can be injected as an IV to improve the imaging of blood vessels by ultrasound. The contrast consists of very fine particles and a method of attaching very small bubbles to the particle. To avoid any associated problems with embolisms the particle and bubbles together are smaller than a typical red blood cell thus allowing the bubbles to pass through from the arteries to the veins. These bubbles are also engineered to not join together as they are formed about a tiny particle rather than free standing bubbles that might have a tendency to enlarge by combining.

The purpose of injecting bubbles into the vasculature is to increase the ultrasonic contrast of the blood by adding well dispersed low density material. Contrast agent is rapidly eliminated in the blood by the breaking of the newly formed bubbles. An unrecognized feature of the contrast agents is that as each bubble breaks it creates a disturbance within the vasculature which is highly localized.

Ultrasound contrast media are already FDA cleared for use in stroke diagnostics and vessel imaging. To ensure the safety of injecting bubbles into the blood the bubble size is very well controlled. Bubbles of the same size have a well-defined and distinctive signature when they break. This consistency allows for precise localization of the resulting signal.

Since the bubbles are smaller than a red blood cell, the bubbles are able to perfuse from the arteries to the veins. The bubbles break randomly over a controlled period of time, typically five to 20 minutes after injection. If the amount of contrast media that is injected is reduced significantly from the amount typically given for ultrasound imaging the number of bubbles that break can be controlled to have, on average, a few milliseconds between bursts. Thus, a system that is sensing the breaks from multiple sensors can localize the position of the bubble when it broke to a few mm or better resolution. Summing over a large number of events will produce a 3D map of where the bubbles have reached.

One of the major objectives of stroke treatment is determining whether a patient has a stroke at all and if they have had a stroke to differentiate an ischemic from a hemorrhagic. This differentiation is critical to caring for the patient. If clot dissolving drugs are used on a hemorrhagic patient the likely outcome is significantly worse, including death, over no treatment at all. Likewise not treating an ischemic stroke patient within the first three hours (for current drugs) of the stroke results in no treatment at all.

A 3D bubble map will show areas that are not perfused, an area with little or no bubbles showing up; the signature of a vessel blockage or ischemic stroke. Aneurysms, the typical cause of hemorrhagic strokes, will show up in both the direct sensor signals and in the 3D bubble map. A lack of perfusion in an area around the aneurysms would be a strong indicator of non-flowing pooled blood. A perfused area distal to the aneurysm would be a further indication of no ischemic stroke. Thus the system would allow rapid, clinically relevant, differentiation of stroke type enabling treatment to be delivered in a timely manner.

An example would be when giving tissue plasminogen activator (tPA) to dissolve a clot. The clot region could be monitored and tPA administered while watching the blood flow and perfusion so that the right amount of tPA is administered. This would be possible even if the patient were not able to indicate physical improvements, i.e., asleep or in a natural or induced coma.

Merger of Data

The sensors 110 deliver data on major unusual events in the vasculature. Merging this data into a "typical" 3D map of the complete vasculature ignores the real differences between individuals. It still provides clinically relevant data, such as lack of blood flow in an area of the brain and then a subsequently reperfusion of that area. This highlights the major advantage of having a continuous monitoring system over a snapshot monitoring such as CT, MRI or contrast angiography.

Adding the bubble map would allow a complete map of the vasculature since the bubbles burst through out all the perfused vessels within the brain. Since the same sensors, and sensor locations, are used to produce both maps, the two data sets can be merged to form a single complete map of the vasculature. In addition, this data set can be merged with the CT scan or other scans to combine the data from each to provide the clinician a better picture of the patient's condition.

The preferred embodiments described above are intended to illustrate the principles of the invention, but not to limit its scope. Other embodiments and variations to these preferred embodiments will be apparent to those skilled in the art and may be made without departing from the spirit and scope of the invention as defined in the following claims.

We claim:

1. A system for non-invasive detection of abnormal cranial conditions, the system comprising:
    three or more accelerometers adapted to be engaged externally at three or more different positions against a patient's head simultaneously;
    wherein each of said three or more accelerometers is configured to measure acceleration of the patient's head at one of said three or more different positions resulting from displacement of the patient's skull at said one of said three or more different positions caused by heartbeat-induced pulsing of blood into cranial vasculature;
    wherein each of said three or more accelerometers is configured to generate signal data responsive to said acceleration of the patient's head at one of said three or more different positions resulting from displacement of the patient's skull at said one of said three or more different positions caused by heartbeat-induced pulsing of blood into cranial vasculature; a processing system connected to said three or more accelerometers,
    wherein said processing system is configured to receive said signal data from all of said three or more accelerometers, digitize and process said signal data from all of said three or more accelerometers in parallel thereby maintaining timing information in said signal data,
    analyze said signal data from all of said three or more accelerometers by determining phase time differences among the signal data from each of said three or more accelerometers,
    match said signal data with known signal data of abnormal cranial conditions to thereby detect abnormal cranial conditions of the patient non-invasively, and generate a display indicative of said abnormal cranial conditions of the patient.

2. The system of claim 1, wherein said processing system is further configured to use said phase time differences among the signal data from each of said three or more accelerometers to perform source signal localization.

3. The system of claim 1, wherein said processing system is further configured to analyze said signal data from all of said three or more accelerometers by correlating said signal data from each of said plurality of accelerometers to determine a waveform signal common to the signal data from all of the three or more accelerometers.

4. The system of claim 1, wherein each of said three or more accelerometers has a sensitivity of at least 500 mV/g.

5. The system of claim 1, wherein said three or more accelerometers comprise four accelerometers engaged externally at four different positions against a patient's head.

6. The system of claim 1, wherein said processing system is configured to receive pulse timing information for use in analyzing said signal data from said three or more accelerometers.

7. The system of claim 1, further comprising:
a pulse sensor which generates pulse timing information; and
wherein said processing system is configured to receive pulse timing information for use in analyzing said signal data from said three or more accelerometers.

8. The system of claim 1, further comprising:
a EKG sensor which generates pulse timing information; and
wherein said processing system is configured to receive pulse timing information for use in analyzing said signal data from said three or more accelerometers.

9. The system of claim 1, further comprising a conditions library for use in detecting the abnormal cranial conditions.

10. The system of claim 1, further comprising: a neural network wherein signal data from said plurality of accelerometers is digitized and processed in parallel through the neural network; and a conditions library for use by the neural network in detecting the abnormal cranial conditions.

11. The system of claim 1, wherein the processing system is configured to differentiate which of a plurality of possible abnormal cranial conditions is indicated in the patient using said signal data from said three or more accelerometers.

12. The system of claim 1, wherein the processing system is configured to continuously monitor a detected abnormal cranial condition of the patient using said signal data from said three or more accelerometers during a time period when a therapy is administered to the patient.

13. A system for non-invasive detection of abnormal cranial conditions, the system comprising:
four accelerometers adapted to be engaged externally at four different positions against a patient's head simultaneously;
wherein each of said four accelerometers has a sensitivity of at least 500 mV/g and is configured to measure acceleration of the patient's head at one of said four different positions resulting from displacement of the patient's skull at said one of said four positions caused by heartbeat-induced pulsing of blood into cranial vasculature;
wherein each of said four accelerometers is configured to generate signal data responsive to said acceleration of the patient's head at one of said four different positions resulting from displacement of the patient's skull at said one of said four positions caused by heartbeat-induced pulsing of blood into cranial vasculature;
a processing system connected to said four accelerometers, wherein said processing system is configured to receive said signal data from all of said four accelerometers, digitize and process said signal data from all of said four accelerometers in parallel thereby maintaining timing information in said signal data, analyze said signal data from all of said four accelerometers by determining phase time differences among the signal data from the four accelerometers, match said signal data with known signal data of abnormal cranial conditions to thereby detect abnormal cranial conditions of the patient non-invasively, and generate a display indicative of said abnormal cranial conditions of the patient.

14. The system of claim 13, wherein said processing system is further configured to use said phase time differences among the signal data from each of said four accelerometers to perform source signal localization.

15. The system of claim 14, wherein said processing system is further configured to analyze said signal data from said four accelerometers by correlating said signal data from said four accelerometers to determine a waveform signal common to the signal data from the four accelerometers.

16. The system of claim 15, further comprising: a neural network wherein signal data from said four accelerometers is digitized and processed in parallel through the neural network; and a conditions library for use by the neural network in detecting the abnormal cranial conditions.

17. A method for non-invasive detection of abnormal cranial conditions, the method comprising: providing three or more accelerometers and a processing system connected to said three or more accelerometers;
engaging the three or more accelerometers externally at three or more different positions against a patient's head simultaneously;
using the three or more accelerometers to measure acceleration of the patient's head at said three or more different positions resulting from displacement of the patient's skull at said three or more different positions caused by heartbeat-induced pulsing of blood into cranial vasculature;
generating signal data responsive to said acceleration of the patient's head said three or more different positions resulting from displacement of the patient's skull at said three or more different positions caused by heartbeat-induced pulsing of blood into cranial vasculature;
receive said signal data at said processing system; digitize and process said signal data from all of said three or more accelerometers in parallel thereby maintaining timing information in said signal data;
analyzing said signal data with said processing system by determining phase time differences among the signal data from the three or more accelerometers; matching said signal data with known signal data of abnormal cranial conditions to thereby detect abnormal cranial conditions of the patient non-invasively, and generating a display indicative of said abnormal cranial conditions of the patient.

18. The method of claim 17, wherein each of said three or more accelerometers has a sensitivity of at least 500 mV/g.

* * * * *